United States Patent [19]

Watson et al.

[11] 4,059,118

[45] Nov. 22, 1977

[54] TOBACCO AND TOBACCO-CONTAINING MANUFACTURES CONTAINING AN INGREDIENT HAVING PHYSIOLOGICAL COOLING ACTIVITY

[75] Inventors: Hugh R. Watson, Wargrave; David G. Rowsell, Staines; John H. D. Browning, Wokingham, all of England

[73] Assignee: Wilkinson Sword Limited, London, England

[21] Appl. No.: 486,651

[22] Filed: July 8, 1974

Related U.S. Application Data

[63] Continuation-in-part of Ser. No. 221,753, Jan. 28, 1972, abandoned.

[51] Int. Cl.$^2$ .............................................. A24B 3/12
[52] U.S. Cl. .................................... 131/8 R; 131/9; 131/17 R; 131/144
[58] Field of Search ...................... 131/17.9, 8, 261 A; 260/631 R; 424/343, 320, 358

[56] References Cited

U.S. PATENT DOCUMENTS

3,644,653 2/1972 Tcheiltcheff ....................... 424/358

FOREIGN PATENT DOCUMENTS

1,065,767 9/1959 Germany ....................... 131/261 A

OTHER PUBLICATIONS

Chem. Abst. Subject Index, 1945–1956, vols. 41–50, pp. 3848s–3849s.

*Primary Examiner*—Robert W. Michell
*Assistant Examiner*—V. Millin
*Attorney, Agent, or Firm*—Leydig, Voit, Osann, Mayer & Holt, Ltd.

[57] ABSTRACT

According to the invention physiological cooling activity is imparted to tobacco and tobacco-containing manufactures, e.g. pipe tobacco and cigarettes by incorporating therein certain cold receptor stimulating derivatives of p-menthane, viz: p-menthane-3-carboxylic acid, its salts and certain esters thereof, and p-menthane-3-carboxamide.

7 Claims, No Drawings

TOBACCO AND TOBACCO-CONTAINING MANUFACTURES CONTAINING AN INGREDIENT HAVING PHYSIOLOGICAL COOLING ACTIVITY

RELATED APPLICATIONS

This application is a continuation-in-part of application Ser. No. 221,753, filed Jan. 28, 1972, now abandoned. It is also related to applications Ser. Nos. 486,675 and 486,652 both filed on July 8, 1974, in the latter of which there is set forth both general directions and thirteen examples of specific methods for preparing the subject compounds.

FIELD OF INVENTION

This invention relates to tobacco and tobacco-containing manufactures containing an ingredient having a physiological cooling effect on the mucous membrances of the mouth, nose and throat when the tobacco is chewed or inhaled (as in the case of snuff) or when the smoke therefrom is inhaled, as during normal smoking.

BACKGROUND OF THE INVENTION AND PRIOR ART

Menthol is well known for its physiological cooling effect on the skin and mucous membrances of the mouth and has been extensively used as a flavouring agent in tobacco for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use in tobacco is circumscribed by its strong minty odour and its relative volatility. For example, it is well known that "mentholated" cigarettes deteriorate quite rapidly on storage.

A few other compounds have been reported in the technical literature as having an odour or flavour similar to methol and from time to time have been proposed as flavourants in tobacco. For example, Japanese Patent Publication No. 39-19627 reports that 3-hydroxymethyl p-menthane (menthyl carbinol) has a flavour closely resembling that of l-menthol and suggests its use as a flavourant in tobacco. In Swiss Pat. No. 484,032 certain saccharide esters of menthol are proposed as additives to tobacco. Other compounds have been reported in the literature as having an odour and physiological cooling effect similar to menthol but without any specific recommendation for their use as additives in tobacco. For example, in French Pat. No. 1,572,332 N,N-Dimethyl 2-ethylbutanamide is reported having a minty odour and refreshing effect, and the minty odour of N,N-diethyl 2,2-dimethylpropanamide is referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl hept-2-en-4-ol in Parfums-Cosmetiques-Savons, May 1956, pp. 17-20. The cooling effect of menthol and other related terpene alcohols and their derivatives has also been studied and reported in Koryo, 95, (1970), pp. 39-43. 2,3-p-menthane diol has also been reported as having a sharp cooling taste (Beilstein, Handbuch der Organischen Chemie, fourth Ed. (1923) Vol. 6, p. 744).

Despite this knowledge of other compounds having an odour and flavour similar to that of menthol, menthol is still extensively used in tobacco notwithstanding the disadvantages mentioned above, namely its very strong odour and its relative volatility.

OBJECTS OF THE INVENTION

It is an object of the present invention to provide tobacco and tobacco containing manufactures containing an ingredient which creates a "cool" sensation when the ingredient comes into contact with the nasal and oral mucosa, either in the tobacco smoke, or by direct contact of the tobacco on the nasal or oral mucosa, but which are not subject to the disadvantages of a strong minty flavour and storage instability.

It is a further object of the present invention to provide an improved method of imparting to tobacco and tobacco-containing manufactures a physiological cooling activity.

SUMMARY OF INVENTION

The present invention is based on the discovery of a group of 3-substituted-p-menthanes which have a pronounced physiological cooling activity, which have little or no odour, which are of relatively low volatility and which are substantially non-toxic. These compounds are 3-substituted-p-menthanes of the formula:

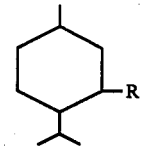

where: R is (i) —$CONH_2$; or (ii) —COOR', where R' is hydrogen; an alkali (eg. Na,K etc) or alkaline earth (eg. Ca,Mg etc) metal atom, or an ammonium or substituted ammonium radical (e.g. trimethylammonium, β-hydroxyethylammonium); or a radical containing from 2 to 10 carbon atoms and selected from hydroxyaliphatic radicals having a hydroxyl substituent in a 2- or 3-position and a hydrogen atom in the 1-position; a lower alkylene oxide (e.g. ethylene oxide, propylene oxide etc) adduct of such a hydroxyaliphatic radical; a ketal derivative of such a hydroxyaliphatic radical with a lower ketone (e.g. acetone); a lower acyl (e.g. acetyl) derivative of such a hydroxyaliphatic radical; a hydroxyaryl radical having a hydroxyl substituent in a 2- or 3-position relative to the ester grouping; a carboxyaliphatic radical having a carboxyl group in a 1-, 2-or 3-position; an alkali metal (e.g. Na,K), alkaline earth metal (e.g. Ca,Mg), ammonium or substituted ammonium (e.g. trimethylammonium, β-hydroxyethylammonium) salt of such a carboxyaliphatic radical; or a lower alkyl (e.g. methyl, ethyl etc.) ester of such a carboxyaliphatic radical.

DEFINITIONS

By 'hydroxyaliphatic' we mean a hydrocarbyl group free of aromatic unsaturation, having a hydroxyl group in the specified position relative to the ester (—COO—) grouping, but being otherwise essentially free of functional groups. Hydroxyaliphatic therefore embraces hydroxyalkyl, hydroxycycloalkyl, hydroxyalkenyl, hydroxyalkynyl, hydroxyalkylcycloalkyl and hydroxycycloalkylalkyl and similar combinations. Particular hydroxyaliphatic groups include 2-hydroxyethyl, 2-hydroxypropyl, 2,3 dihydroxypropyl, sorbityl, 2-hydroxycyclohexyl, 2-hydroxycyclohexylmethyl, 2-hydroxy-4-methylcyclohexyl, 2-hydroxy-1,2-dimethylethyl, and 2-hydroxy-1-methylethyl etc.

By 'carboxyalophatic' we mean a hydrocarbyl group free of aromatic unsaturation, having a carboxyl group in the specified position relative to the ester (—COO—) grouping but being otherwise essentially free of functional groups. Carboxyaliphatic therefore includes carboxyalkyl, carboxycycloalkyl, carboxyalkenyl, carboxyalkynyl, carboxyalkylcycloalkyl, carboxycycloalkylalkyl and similar combinations. Typical carboxyaliphatic groups include 1-carboxyethyl, 2-carboxyethyl, 2-carboxypropyl, 3-carboxypropyl, 3-carboxypropenyl, 3-carboxypropynyl, 2-carboxycyclohexyl, 2-carboxycyclohexylmethyl, 4-methyl-2-carboxycyclohexyl etc.

By 'hydroxyarly' we mean a hydrocarbyl group containing aromatic unsaturation, having a hydroxyl group in the specified position relative to the ester (—COO—) grouping, but being otherwise essentially free of functional groups. Hydroxyaryl therefore includes aralkyl, alkaryl and like combinations. As indicated, the hydroxyaryl group will contain a hydroxyl group in a 2- or 3-position relative to the ester grouping; this may be a nuclear hydroxyl group as in ortho-hydroxybenzyl, orthohydroxyphenyl or orthohydroxynaphthyl or in a side chain as in 1-phenyl-2-hydroxyethyl or o-(hydroxymethyl) phenyl.

By 'substituted ammonium' in all instances we mean salts with organic amines, and in particular alkylamines e.g. mono-,di-and trialkylamines and alkanolamines e.g. ethanolamine.

By 'lower' in all instances we mean containing from 1-4 carbon atoms.

By 'essentially free' of functional groups in all instances we mean free of substituent groups such as amino, alkylamino, alkoxy, acyloxy in positions which interfere with the physiological cooling activity.

STATEMENT OF INVENTION

According to the present invention therefore, there are provided tobacco and tobacco-containing manufactures comprising tobacco and a cold receptor stimulating additive, present in an amount effective to stimulate the cold receptors of the nervous system of mucous membranes of the oral and nasal mucosa when the tobacco or tobacco-containing manufacture is smoked, chewed or inhaled by the human, user, said additive being a cold receptor stimulating 3-substituted-p-menthane of the formula hereinbefore defined.

By tobacco and tobacco-containing manufactures we mean any article, such as a cigarette or cigar, or any composition, such as pipe or chewing tobacco or snuff, containing tobacco in a prepared form ready for utilisation by the human person whether by smoking, i.e. burning of the prepared tobacco and inhalation of the tobacco smoke, chewing or direct inhalation of the tobacco.

The compounds used as cold receptor stimulants in accordance with this invention exhibit both geometric and optical isomerism and, depending on the starting materials and the methods used in their preparation the compounds may be isomerically pure, i.e. consisting of one geometric or optical isomer, or they may be isomeric mixtures, both in the geometric and optical sense.

As is well known, the basic p-methane structure is a chair-shaped shaped molecule which can exist in cis or trans forms. Substitution of the carboxyl or amide group into the 3-position gives rise to four configurational or geometric isomers depending upon whether the substitution is axially or equatorially into the cis or trans isomer, the four isomers being related as menthol is to neomenthol, isomenthol, and neoisomenthol. In general it is found that in the compounds used in this invention the equatorially substituted derivatives have the greater cooling effect than the axial compounds and are to be preferred.

Substitution of the carboxyl or amide group in the 3-position of the p-menthane structure also gives rise to optical isomerism, each of the above-mentioned four geometric isomers, existing in d, l and dl forms. The physiological cooling effect is found, in most cases, to be greater in the l-form than in d-form, and in some cases substantially greater. The l-acid and derivatives of the l-acid are therefore preferred.

The cooling sensation created by the compounds used in this invention on the skin and mucous membrances, for example, in the mouth, varies both in intensity and longevity from compound to compound.

In general, the preferred compounds are the acid, i.e. the compound where R is COOH; the amide, i.e. where R = CONH$_2$; the 2hydroxy (lower) alkyl esters, i.e. where R is COOR', with R' being a lower alkyl group with a hydroxy substituent in the 2position, and particularly the 2-hydroxyethyl ester.

For the purpose of the present disclosure the following test procedure has been devised as a means to identify compounds having a physiological cooling activity in accordance with the present invention and herein referred to as cold receptor stimulant. This test is intended purely as a means for identifying compounds having a physiological cooling activity and useful in the present invention and for giving an indication of the different relative activities of the compounds, as between themselves and as compared with menthol. The test is not intended as anything more than a very rough guide in the choice of cold receptor stimulant to be used in any particular tobacco or tobacco containing manufacture where other factos will come into play. For example, different compounds will be more suitable for incorporation into cigarettes, particularly if simply deposited on a filter tip, than in pipe tobacco, chewing tobacco or snuff. Similarly, different compounds will be more suited to incorporation in pipe tobacco and chewing tobacco. The formulation of actual products according to this invention will therefore be done largely on an empirical basis although the test results and other figures given herein will be useful as a guide, particularly in the formulation of chewing tobacco, since the test procedure to be described involves oral application of the compound.

It will also be noted that the described test procedure is done on a statistical basis. This is necessary since sensitivity to these compounds will vary from one individual to another. Tests of this nature are commonly used in the testing of the organoleptic properties, e.g. taste, smell, etc. of organic and inorganic compounds, see Kirk-Othmer: Encyclopedia of Chemical Technology, Second Ed. (1967) Vol. 14 pages 336–344.

TEST PROCEDURE

The following test procedure is aimed at determining the minimum quanity of the test compound required to produce a noticeable cooling effect on a person of average sensitivity, this minimum quantity being termed the threshold for that particular compound. The tests are carried out on a selected panel of 6 people of median sensitivity to 1-menthol.

PANEL SELECTION

To select a test panel of average sensitivity the following procedure is used. Known quantities of 1-menthol in solution in petroleum ether (bp. 40-60) are placed on 5 mm. squares of filter paper, whereafter the solvent is allowed to evaporate. A panel of observers is enrolled and asked to place one impregnated square at a time on the tongue and to report on the presence or absence of a cooling effect. The quantity of 1-menthol on each impregnated square is gradually reduced from a value substantially above 0.25 $\mu$g. per square to substantially below 0.25 $\mu$g. the precise range being immaterial. Conveniently, one starts with squares containing 2.0 $\mu$g. 1-menthol, the amount on each successive square being half that of the preceding square, i.e. the second test square will contain 1.0 $\mu$g, the third 0.5 $\mu$g and so on. Each quantity is tested on the tongue at least 10 times. In this way, the thresholds to cold receptor stimulus by 1-methol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 $\mu$g to 10 $\mu$g and whose average threshold is approximately 0.25 $\mu$g., this select panel being regarded as the test panel of average sensitivity.

COMPOUND TESTING

To test the activity of compounds according to this invention, the above procedure is repeated using only the 6 selected panel members of average sensitivity to 1-methol. The individual thresholds for each test compound on each of the 6 selected panel members are determined and averaged. Those compounds whose average threshold on the select test panel is 100 $\mu$g or less are regarded as having cooling activity in accordance with this invention.

TEST RESULTS

The following table sets out the relative cooling activities of compounds of the formula defined above when tested according to the foregoing procedure.

TABLE

| Compound | Threshold ($\mu$g) |
| --- | --- |
| p-menthane-3-carboxylic acid | 4 |
| p-menthane-3-carboxylic acid ammonium salt | 5 |
| p-menthane-3-carboxylic acid sodium salt | 4 |
| p-menthane-3-carboxylic acid ethanolamine salt | 6 |
| p-menthane-3-carboxamide | 20 |
| p-menthane-3-carboxylic acid esters where ester moiety equals: | |
| —CH$_2$CH$_2$OH | 1.5 |
| —CH$_2$CH(OH)CH$_2$OH | 1.2 |
| —CH$_2$CH(OH)CH$_3$ } Isomeric mixture | 1.4 |
| —CH(CH$_2$OH)CH$_3$ | |
| —CH$_2$(CHOH)$_4$CH$_2$OH | 50 |
| —CH$_2$CH$_2$OCOCH$_3$ | 33 |
| —CH$_2$CH$_2$CH$_2$OH | 7 |
| —CH(CH$_3$)CH(CH$_3$)OH | 3 |
| —CH$_2$CH(OH)n-C$_4$H$_9$ } Isomeric mixture | 8 |
| —CH(CH$_2$OH)n-C$_4$H$_9$ | |
| —CH$_2$CH(OH)n-C$_8$H$_{17}$ | 90 |
| —CH$_2$(CHOH)$_2$CH$_2$OH | 50 |
| —CH$_2$CH$_2$(OCH$_2$CH$_2$)$_2$OH | 5 |
| —CH$_2$CH$_2$OCH$_2$CH$_2$OH | 1.0 |
| —CH$_2$CH$_2$(OCH$_2$CH$_2$)$_{2.75}$OH | 15 |
| —phenyl (hydroxyphenyl) | 5 |
| —cyclohexyl (hydroxycyclohexyl) | 4 |
| —methylphenyl-OH | 15 |
| —CH$_2$—CH—CH$_2$ with O—C(CH$_3$)$_2$—O acetonide | 11 |
| —CH(CH$_3$)COOH | 8 |
| —CH$_2$CH$_2$COOH | 10 |
| —C(CH$_3$)$_2$COOH | 20 |
| —CH(CH$_3$)COOC$_2$H$_5$ | 50 |
| —CH$_2$COOH | 15 |

In formulating the tobacco and tobacco-containing manufactures of this invention the active compound may be incorporated directly into the tobacco, for example, by impregnation of the tobacco with an alcoholic solution of the active ingredient, at a suitable stage of manufacture. However, in an alternative and preferred arrangement, the active ingredient may be incorporated into a tobacco smoke filter for use in a pipe or cigarette filter or as a filter tip for cigarettes. The latter, in particular, forms a particularly effective utilisation of the present invention, the active compound simply being inpregnated in the wad of material forming the filter tip. This may be of any of the well known types of filter tip for cigarettes, e.g. a filter pad of cellulose acetate, paper, cotton, $\alpha$-cellulose or asbestos fiber. Conveniently the filter tip is impregnated with an alcoholic solution of the active compound and then dried to deposit the active compound therein.

The amount of active compound to be incorporated into the tobacco or tobacco-containing manufacture in accordance with the invention will vary from compound to compound depending on the activity thereof, i.e. the amount thereof which it is necessary to place in contact with the skin to produce a noticeable cooling effect, and will depend also on the mode of application thereof, i.e. whether the compound is impregnated in the tobacco itself, or in a filter tip or in any other accessory. However, the actual amount is not critical to this invention and will be readily determinable by the person skilled in the art by means of a few simple tests. As a matter of guidance, however, it may be mentioned that with the more active compounds, as little as 0.01 mg. deposited on the filter tip of a tipped cigarette is effective.

The invention is illustrated by the following Examples.

EXAMPLE 1

Cigarette Tobacco

A proprietary brand of cigarette tobacco was sprayed with an ethanolic solution of p-menthane-3-carboxamide and was rolled into cigarettes each containing approximately 5.0 micrograms of active compound. Smoking the inpregnated cigarettes produced a cool effect in the mouth characteristic of mentholated cigarettes but without any attendant odour other than that normally associated with tobacco.

EXAMPLE 2

Filter Tip Cigarettes

The filter tip of a proprietary brand of cigarette was impregnated with an ethanolic solution of p-menthane-3-carboxylic acid in an amount sufficient to deposit in the filter 0.02 mg. of the active compound. Smoking the cigarette with the impregnated tip give rise to a noticeable cooling effect in the mouth.

EXAMPLE 3

Pipe Tobacco

A proprietary brand of pipe tobacco was sprayed with an ethanolic solution of 2-hydroxyethyl p-menthane-3-carboxylate. 2g. of the tobacco, containing 8mg. of the active compound was placed in a pipe. Smoking the impregnated tobacco produced a cool effect in the mouth characteristic of mentholated tobacco but without any attendant odour other than that normally associated with tobacco.

EXAMPLE 4

Cigars

The tobacco of a proprietary brand of cigar was impregnated with an ethanolic solution of 2-hydroxyethyl p-menthane-3-carboxylate in an amount sufficient to deposit in the cigar 10mg. of the active compound. Smoking the cigar with the impregnated tobacco gave rise to a noticeable cooling effect in the mouth.

EXAMPLE 5

Chewing Tobacco

A proprietary brand of chewing tobacco was impregnated with an ethanolic solution of 1-(p-menth-3-oyl)-glycerol. 1g. of the tobacco containing 0.5mg. of active compound was used. Chewing the impregnated tobacco produced a cool effect in the mouth.

EXAMPLE 6

Snuff

A proprietary brand of snuff was impregnated with an ethanolic solution of 3-hydroxypropyl p-menthane-3-carboxylate. 1g. of the snuff was impregnated with 4mg. of active compound. About 0.01g. of the impregnated snuff produced a cool effect in the nose when inhaled.

We claim:

1. A tobacco or tobacco-containing manufacture comprising tobacco and an agent capable of stimulating the cold receptors of the nervous system of the nasal or oral mucosa when brought into contact therewith upon use of the manufacture, wherein said agent comprises an effective amount of a cold receptor stimulating substituted p-menthane of the formula:

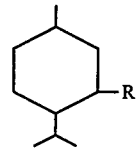

where: R is (i)—CONH$_2$; or (ii)—COOR', where R' is hydrogen; an alkali or alkaline earth metal atom, or an ammonium or substituted ammonium radical; or a radical containing from 2 to 10 carbon atoms and selected from hydroxyaliphatic radicals having a hydroxyl substituent in a 2- or 3-position and a hydrogen atom in the 1-position; a ketal derivative of such a hydroxyalophatic radical with a lower ketone; a lower acyl derivative of such a hydroxyaliphatic radical; a hydroxyaryl radical having a hydroxyl substituent in a 2- or 3-position relative to the ester grouping; a carboxyaliphatic radical having a carboxyl group in a 1-, 2- or 3-position; an alkali metal, alkaline earth metal, ammonium or substituted ammonium salt of such a carboxyaliphatic radical; a lower alkyl ester of such a carboxyaliphatic radical; and a lower alkylene oxide adduct of a hydroxyaliphatic radical having a hydroxyl substituent in a 2- or 3-position and a hydrogen atom in the 1-position.

2. A manufacture according to claim 1, wherein said stimulant is of the formula defined, where R is CONH$_2$, COOH or COOR', where R' is selected from hydroxyalkyl radicals containing from 2–4 carbon atoms inclusive and having a hydroxyl substituent in the 2-position.

3. Tobacco impregnated with an amount of a cold receptor stimulant effective to stimulate the cold receptors of the nervous system of the oral or nasal mucosa when said tobacco, or the smoke therefrom, is in contact therewith, wherein said stimulant is a cold receptor stimulating 3-substituted-p-menthane of the formula defined in claim 1.

4. A cigarette containing an amount of a cold receptor stimulant effective to stimulate the cold receptors of the nervous system of the oral or nasal mucosa when the cigarette is smoked, wherein said stimulant is a cold receptor stimulating 3-substituted-p-menthane of the formula defined in claim 1.

5. A filter-tipped cigarette comprising a filter tip, a tobacco-containing body, and an amount of a cold receptor stimulant effective to stimulate the cold receptors of the nervous system of the oral or nasal mucosa when the cigarette is smoked, wherein said stimulant is a cold receptor stimulating 3-substituted-p-menthane of the formula defined in claim 1 which is impregnated in said filter tip.

6. A method of stimulating the cold receptors of the nervous system of the nasal and oral mucosa which comprises contacting said mucosa with an effective amount of a cold receptor stimulating 3-substituted-p-menthane of the formula defined in claim 1, entrained in a stream of tobacco smoke.

7. A method of imparting to tobacco and tobacco-containing manufactures the property of stimulating the cold receptors of the nervous system of oral or nasal mucosa when in contact therewith, or when the smoke therefrom is inhaled, which comprises incorporating therein an effective amount of a cold receptor stimulating 3-substitued-p-menthane of the formula defined in claim 1.

* * * * *